(12) United States Patent
Bordier et al.

(10) Patent No.: US 7,126,007 B2
(45) Date of Patent: Oct. 24, 2006

(54) PROCESS FOR PREPARING PYRROLIDINYL-FUNCTIONAL PARA-PHENYLENEDIAMINE DERIVATIVES SUBSTITUTED BY A NITROGENOUS RADICAL, AND INTERMEDIATE COMPOUNDS

(75) Inventors: Thierry Bordier, Trembay en France (FR); Jinzhu Xu, Paris (FR)

(73) Assignee: L'Oreal S.A., Paris (FR)

( * ) Notice: Subject to any disclaimer, the term of this patent is extended or adjusted under 35 U.S.C. 154(b) by 134 days.

(21) Appl. No.: 10/995,558

(22) Filed: Nov. 24, 2004

(65) Prior Publication Data

US 2005/0209466 A1 Sep. 22, 2005

(30) Foreign Application Priority Data

Nov. 28, 2003 (FR) .................. 03 50939

(51) Int. Cl.
*C07D 403/04* (2006.01)
*C07D 207/14* (2006.01)
*C07D 401/04* (2006.01)

(52) U.S. Cl. .................. 548/314.7; 548/557; 546/208; 546/279.1

(58) Field of Classification Search ............. 548/314.7, 548/557; 546/279.1, 208
See application file for complete search history.

(56) References Cited

U.S. PATENT DOCUMENTS

| | | | |
|---|---|---|---|
| 4,855,292 A | 8/1989 | Ueda et al. | |
| 4,874,764 A | 10/1989 | Ueda et al. | |
| 4,880,806 A | 11/1989 | Ueda et al. | |
| 4,935,420 A | 6/1990 | Ueda et al. | |
| 2002/0106341 A1 | 8/2002 | Lim et al. | |
| 2003/0093866 A1 | 5/2003 | Vidal et al. | |

FOREIGN PATENT DOCUMENTS

| | | |
|---|---|---|
| FR | A-2 603 584 | 3/1988 |
| JP | A-02-264 735 | 10/1990 |
| WO | WO 96/13502 | 5/1996 |
| WO | WO 98/01426 | 1/1998 |
| WO | WO 99/64417 | 12/1999 |
| WO | WO 00/23447 | 4/2000 |
| WO | WO 01/29011 A3 | 4/2001 |
| WO | WO 01/68043 A3 * | 9/2001 |
| WO | WO 02/018383 A3 | 3/2002 |
| WO | WO 02/45675 A1 | 6/2002 |

OTHER PUBLICATIONS

Yen-Lin Huang et al, "*Non-classical Antifolates, 5-(N-Penylpyrolidin-3-yl)-2,4,6-triaminopyrimidines and 2,4-Diamino-6(5H)-oxopyrimidines, Synthesis and Antitumor Studies.*" Bioorganic & Medicinal Chemistry 11 (2003) 145-157.
French Search Report for FR 03 50939 (French Priority Application for U.S. Appl. No. 10/995,558, the present application) dated Jul. 16, 2004, Examiner Seitner.
English language Abstract for JP 02-264735.

* cited by examiner

*Primary Examiner*—Kamal A. Saeed
*Assistant Examiner*—Michael P. Barker
(74) *Attorney, Agent, or Firm*—Finnegan, Henderson, Farabow, Garrett, Dunner, LLP

(57) ABSTRACT

A process for synthesizing para-phenylenediamine derivative compounds containing a pyrolidinyl group, and substituted by a nitrogenous radical, wherein the para-phenylenediamine derivative compounds are chosen from those of formula (I):

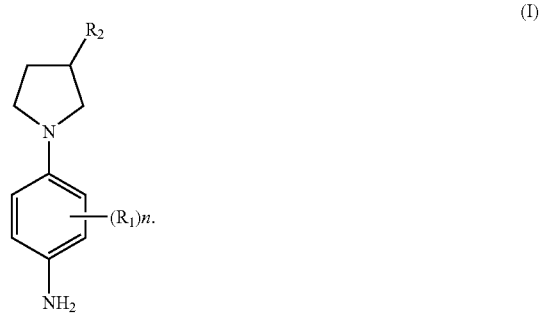

Intermediates containing a pyrrolidinyl group bearing a nitrogenous radical are also disclosed herein.

22 Claims, No Drawings

PROCESS FOR PREPARING PYRROLIDINYL-FUNCTIONAL PARA-PHENYLENEDIAMINE DERIVATIVES SUBSTITUTED BY A NITROGENOUS RADICAL, AND INTERMEDIATE COMPOUNDS

The invention relates to a synthesis process for preparing para-phenylenediamine derivatives containing a pyrrolidinyl group and substituted by a nitrogenous radical.

It likewise pertains to intermediate compounds containing a pyrrolidinyl group bearing a nitrogenous radical.

The para-phenylenediamine derivatives containing a pyrrolidinyl group which can be prepared by the process of the invention correspond for example to the formula (I) below:

formula (I)

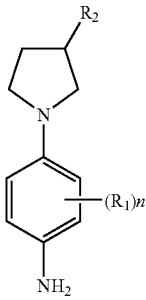

in which:
- the carbon bearing the substituent $R_2$ on the pyrrolidine ring is racemic or chiral;
- n is an integer from 0 to 4, on the understanding that, when n is greater than or equal to 2, the radicals $R_1$ can be identical or different;
- $R_1$ represents a halogen atom; a saturated or unsaturated, $C_3$ to $C_8$ alicyclic or $C_1$ to $C_6$ aliphatic hydrocarbon chain; it being possible for one or more carbon atoms of the chain to be replaced by an oxygen, nitrogen, silicon or sulfur atom or by an $SO_2$ group; the radical $R_1$ not containing a peroxide linkage, nor diazo, nitro or nitroso radicals;
- $R_2$ represents a cationic or noncationic nitrogenous radical.

The para-phenylenediamine derivative compounds containing a pyrolidinyl group which are substituted by a nitrogenous radical, of the formula (I), are used as an oxidation base for dyeing and in hair dyeing kits and have the advantage of exhibiting a favorable toxicological profile.

Some of the compounds of the formula (I) have been synthesized.

Thus document WO-A-0168043 describes some synthesis examples of certain compounds encompassed by the formula (I), which use a condensation reaction of para-fluoronitrobenzene with a pyrrolidine already substituted by a nitrogenous group (scheme 1).

Scheme 1

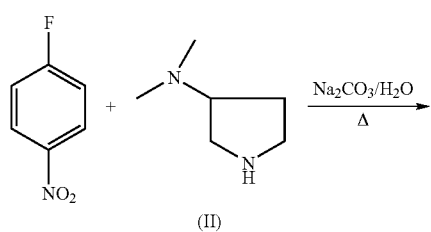

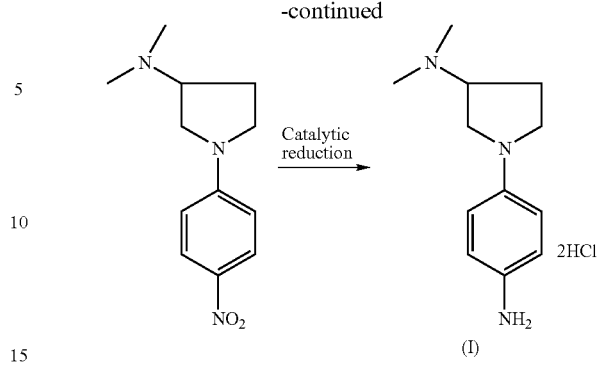

The pyrrolidine derivatives of the type employed as a starting compound in scheme 1, however, such as 3-(N,N-dimethylamino)pyrrolidine, are of low availability and of high expense. Their preparation is not easy and requires a laborious development. A problem therefore arises of the industrial-scale manufacture of these compounds and, consequently, of the compounds of formula (I).

In document WO-A-0245675 cationic derivatives encompassed by the formula (I) were prepared according to scheme 2 below from a precursor of the formula (III) which already possesses the pyrrolidinyl group substituted by an amine group.

Scheme 2

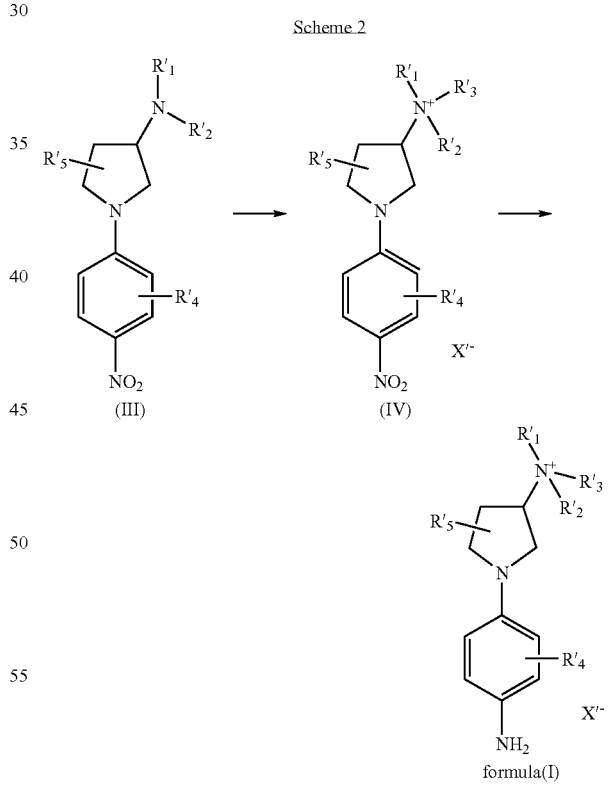

The starting materials of the synthesis according to scheme 2, i.e., the compounds of the formula (III), are not commercial compounds and are not readily obtainable chemically. The end para-phenylenediamines are therefore either expensive or are not industrial products.

It is, moreover, possible to carry out the synthesis of a para-phenylenediamine containing a pyrrolidinyl group substituted by an imidazolinium radical, which is a compound encompassed by the formula (I), from an alcohol of the formula (V). This alcohol is obtained by a substitution reaction of 3-pyrrolidinol with para-fluoronitrobenzene. The alcohol is subsequently converted to a methanesulfonate derivative and then condensed with N-methylimidazole to form the imidazolinium of the formula (VI) (scheme 3).

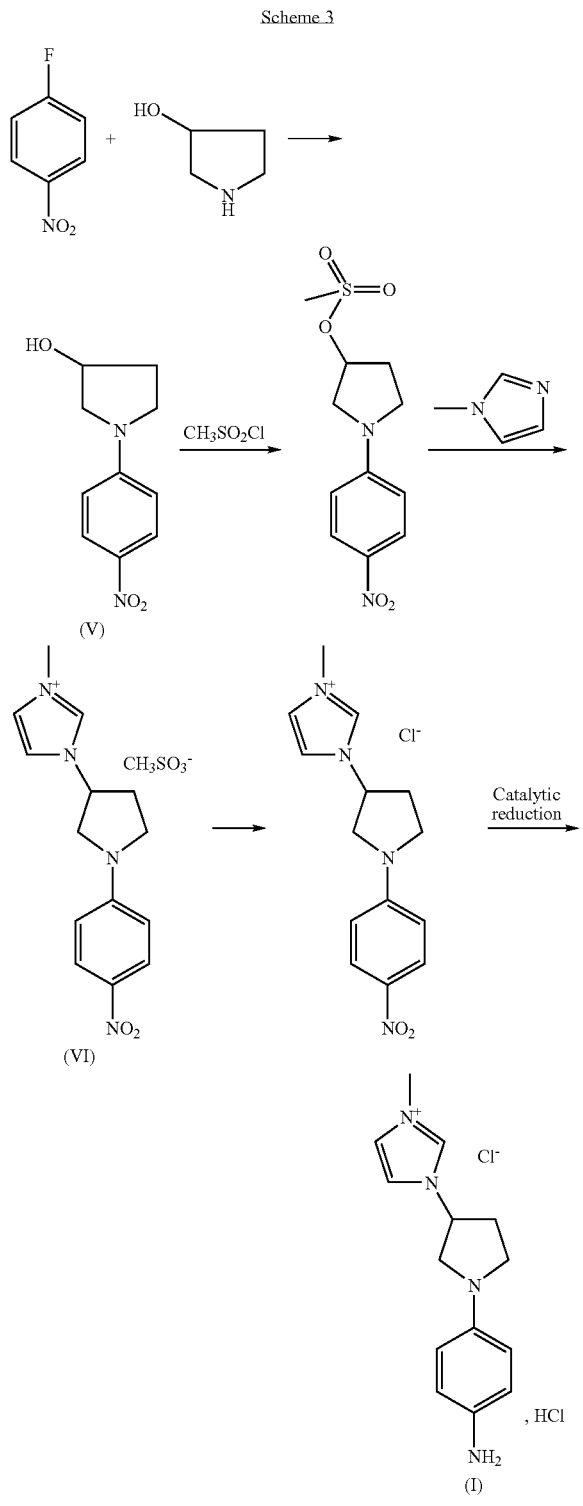

The drawback of this synthesis is that 3-pyrrolidinol is an expensive starting material whose industrial availability is low.

All of the abovementioned preparation processes employ synthesis processes which use starting materials or primary products of low availability or high expense.

In light of the above there exists a need for a process for preparing para-phenylenediamine derivatives or compounds containing a pyrrolidinyl group and substituted by a nitrogenous radical, corresponding in particular to the formula (I) above, which is easy to implement, reproducible and industrially viable.

There also exists a need for a process for preparing these compounds, derivatives, which uses starting materials or primary products which are readily available and of a low cost and which allows the end para-phenylenediamine compounds containing a pyrrolidinyl group to be obtained with a good yield.

There exists in particular a need for a process of this kind which avoids in particular the use, as starting materials, of the precursors of the formulae (II) and (III) or of 3-pyrrolidinol, which are compounds which are expensive and/or are unavailable or of low availability industrially.

The object of the present invention is to provide a synthesis process, for para-phenylenediamine derivative compounds containing a pyrrolidinyl group and substituted by a nitrogenous radical, which, among other things, meets the needs set out above.

The object of the present invention is, further, to provide a process for preparing para-phenylenediamine derivative compounds, containing a pyrolidinyl group and substituted by a nitrogenous radical, which does not exhibit the drawbacks, defects, limitations and disadvantages of the prior art processes and which solves the problems of the prior art processes.

This object and other, further objects are achieved in accordance with the invention by a process for synthesizing para-phenylenediamine derivative compounds containing a pyrrolidinyl group and substituted by a nitrogenous radical which corresponds to the formula (I) below:

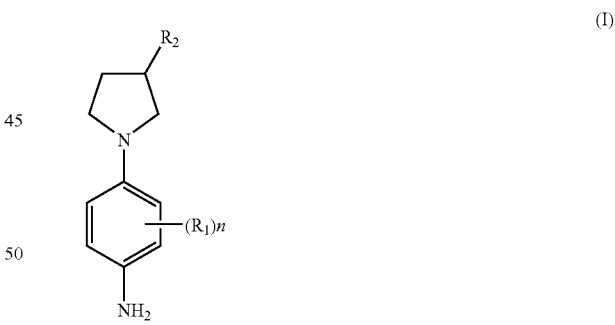

in which:
the carbon bearing the substituent $R_2$ on the pyrrolidine ring is racemic or chiral, i.e., of (R) or (S) configuration;
n is an integer from 0 to 4, on the understanding that, when n is greater than or equal to 2, the radicals $R_1$ can be identical or different;
$R_1$ represents a halogen atom; a saturated or unsaturated, $C_3$–$C_8$ alicyclic, or $C_1$–$C_6$ linear or branched aliphatic, hydrocarbon chain, an aryl radical, an arylalkyl radical in which the alkyl chain is $C_1$–$C_6$, it being possible for one or more carbon atoms of the hydrocarbon chain and of the alkyl chain of the arylalkyl radical to be replaced by an oxygen, nitrogen, silicon or sulfur atom or by an $SO_2$ group; the radical $R_1$ not containing a peroxide linkage, nor diazo, nitro or nitroso radicals;

$R_2$ represents a cationic or noncationic nitrogenous radical;

wherein the following successive steps are carried out:

a) a para-substituted aniline of the formula (VII):

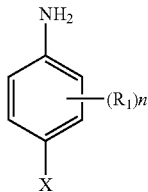
(VII)

in which $R_1$ and n have the meaning already given above for the formula (I), and X represents a precursor group of an amine function, is condensed with a derivative of the formula (VIII):

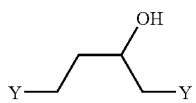
(VIII)

in which Y represents a leaving group, to give a compound of the formula (IX):

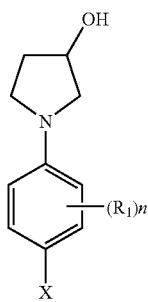
(IX)

in which $X_1$, $R_1$ and n have the meaning already given above;

b) the compound of the formula (IX) is activated, to give a compound of the formula (X):

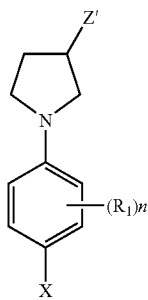
(X)

in which X, $R_1$ and n have the meaning already given above and Z' represents a leaving group;

c) the compound of formula (X) is reacted with ammonia or a primary, secondary or tertiary amine, or with a compound bearing a nitrogen-containing aromatic heterocycle;

to give a compound of the formula (XI):

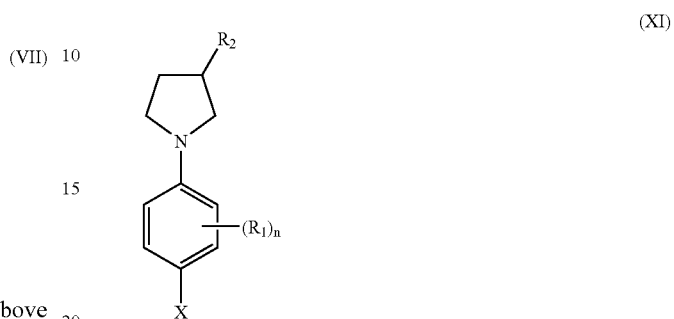
(XI)

in which X, $R_1$, $R_2$ and n have the meaning already given above; and d) the group X is converted to an amine function, to give the compound of the formula (I).

The various steps of the process according to the invention are illustrated in simplified form in scheme 5, given later on below.

The process according to the invention employs starting products (VII) and (VIII) which are readily available industrially and are of a low cost. For example, 1,4-dibromobutanol, encompassed by the formula (VIII), can easily be prepared from 1,2,4-butanetriol according to document JP-A-02 264735.

The process according to the invention, unlike the prior art processes, does not make use of precursors of formulae (II) and (III) or of 3-pyrolidinols as starting materials, and therefore one of the major drawbacks of the prior art processes is avoided.

The process according to the invention is a process which is easy to implement, is reproducible and is industrially viable.

The invention additionally relates, as new compounds, to some of the intermediates of the formula (IX) and of the formula (XI), given above in the context of the description of the process. These new compounds are compounds which correspond to the abovementioned formula (IX) or to the abovementioned formula (XI) in which the group X represents an amide or carbamate group, a nitro group (in the case of the compounds of the formula (IX)) or a nitroso group; more particularly X represents a group —NHCOR or —NHCOOR, a nitroso group or a nitro group (in the case of the compounds of the formula (IX)), where R represent a saturated or unsaturated, preferably saturated, linear or branched $C_1$–$C_6$ aliphatic chain, an aryl group or an arylalkyl group whose alkyl moiety is $C_1$–$C_6$; with the exception (apart from the compounds where X=nitro in the formula (XI)) of certain specific compounds set out later on below.

It should be noted that, in the context of the definition of the compounds (IX) and (XI) given in relation to the process in which they are employed, no specific compound is excluded and X can be $NO_2$ in the formula (XI).

The invention will now be described in greater detail below:

In the context of the invention an aliphatic hydrocarbon chain is a linear or branched chain which may contain unsaturations of the alkene or alkyne type. An alicyclic hydrocarbon chain is a saturated or unsaturated cyclic chain which does not contain an aromatic cyclic structure.

When the chain is interrupted by an oxygen, sulfur, nitrogen or silicon atom Y' or $SO_2$ the result, for example, is a $CH_2$—Y'—$CH_2$.

In the formula (I) n can be 0 and in that case the benzene ring does not bear any substituent. In the opposite case (n other than 0 and, for example, 1) and by way of example $R_1$ may be a chlorine atom or a methyl, ethyl, isopropyl, hydroxymethyl methoxymethyl, hydroxyethyl, 2-hydroxyethyl, 3-hydroxypropyl, 1,2-dihydroxyethyl, methoxy, ethoxy, 2-hydroxyethyloxy or phenyl radical.

As mentioned earlier, in the formula (I), where n is other than zero and is, for example, 1, $R_1$ is a halogen atom; a saturated or unsaturated, $C_3$ to $C_8$ alicyclic, or $C_1$ to $C_6$ linear or branched, aliphatic hydrocarbon chain, an aryl radical, an arylalkyl radical whose alkyl chain is $C_1$–$C_6$, it being possible for one or more carbon atoms of the hydrocarbon chain and of the alkyl chain of the arylalkyl radical to be replaced by an oxygen, nitrogen, silicon or sulfur atom or by an $SO_2$ group; the radical $R_1$ not containing a peroxide linkage, nor diazo, nitro or nitroso radicals.

Preferably, when n is other than 0, and is for example 1, $R_1$ is selected from chlorine, bromine and a $C_1$–$C_4$ alkyl, $C_1$–$C_4$ hydroxyalkyl, $C_1$–$C_4$ aminoalkyl, $C_1$–$C_4$ alkoxy and $C_1$–$C_4$ hydroxyalkoxy radical.

By way of preferred examples $R_1$ is selected from a methyl, hydroxymethyl, 2-hydroxyethyl, 1,2-dihydroxyethyl, methoxy, isopropyloxy and 2-hydroxyethoxy radical.

As indicated earlier the radical $R_2$ represents a cationic or noncationic nitrogenous radical.

If $R_2$ is a cationic nitrogenous radical it represents more particularly an onium radical such as, for example, an ammonium, imidazolium or pyridinium radical.

If $R_2$ is a noncationic nitrogenous radical it represents more particularly a primary (—$NH_2$), secondary (—NHR) or tertiary (—$NR_2$) amine radical where R, which are identical or different, represent a saturated or unsaturated, linear or branched $C_1$–$C_{22}$ aliphatic radical, preferably a $C_1$–$C_{22}$ alkyl radical; a saturated or unsaturated $C_3$–$C_8$ alicyclic radical; a $C_1$–$C_{22}$, preferably $C_1$–$C_6$, monohydroxyalkyl radical; a $C_2$–$C_{22}$, preferably $C_2$–$C_6$, polyhydroxyalkyl radical; a ($C_1$–$C_6$-alkoxy)($C_1$–$C_{22}$, preferably $C_1$–$C_6$-)alkyl radical; an aryl radical; an arylalkyl radical whose alkyl moiety is $C_1$–$C_6$, such as the benzyl radical, for example; an amido($C_1$–$C_6$-alkyl) radical; a tri($C_1$–$C_6$-alkyl)silane($C_1$–$C_6$-alkyl) radical; a $C_1$–$C_6$ aminoalkyl radical; or a $C_1$–$C_6$ aminoalkyl radical whose amine is mono- or di-substituted by a $C_1$–$C_4$ alkyl, ($C_1$–$C_6$-alkyl)carbonyl, amido or ($C_1$–$C_6$-alkyl)sulfonyl radical.

Furthermore, the radicals R may form, in pairs, together with the nitrogen atom to which they are attached, a saturated carbon ring containing 3 to 9 members, preferably 4, 5, 6, 7 or 8 members, which may contain one or more heteroatoms. As examples of such rings mention may be made of azetidine, pyrrolidine, piperidine, piperazine and morpholine rings, it being possible for said heterocycle to be substituted by a halogen atom, an hydroxyl radical, a $C_1$–$C_6$ alkyl radical, a $C_1$–$C_6$ monohydroxyalkyl radical, a $C_2$–$C_6$ polyhydroxyalkyl radical, a $C_1$–$C_6$ alkoxy radical, a tri($C_1$–$C_6$-alkyl)silane($C_1$–$C_6$-alkyl) radical, an amido radical, a carboxyl radical, a ($C_1$–$C_6$-alkyl)carbonyl radical, a thio (—SH) radical, a $C_1$–$C_6$ thioalkyl (—R—SH) radical, a ($C_1$–$C_6$-alkyl)thio radical, an amino radical, or an amino radical mono- or di-substituted by a ($C_1$–$C_6$)alkyl, ($C_1$–$C_6$-alkyl)carbonyl, amido or ($C_1$–$C_6$-alkyl)sulfonyl radical.

In accordance with another embodiment $R_2$ is a radical derived from aminoguanidine (of the formula —NH—NH—C($NH_2$)=NH).

If the radical $R_2$ of the formula (I) (and (XI)) is an onium radical Z it corresponds in a first embodiment to the formula (XIII):

(XIII)

in which:

$R_3$, $R_4$ and $R_5$, taken separately, which are identical or different, represent a hydrogen atom, a saturated or unsaturated, linear or branched $C_1$–$C_{22}$ aliphatic radical, preferably a $C_1$–$C_{22}$ alkyl radical; a saturated or unsaturated $C_3$–$C_8$ alicyclic radical; a $C_1$–$C_{22}$, preferably $C_1$–$C_6$ monohydroxyalkyl radical; a $C_2$–$C_{22}$, preferably $C_2$–$C_6$ polyhydroxyalkyl radical; a ($C_1$–$C_6$-alkoxy) ($C_1$–$C_{22}$, preferably $C_1$–$C_6$-alkyl) radical; an aryl radical; an arylalkyl radical whose alkyl moiety is $C_1$–$C_6$, such as the benzyl radical, for example; an amido($C_1$–$C_6$-alkyl) radical; a tri($C_1$–$C_6$-alkyl)silane ($C_1$–$C_6$-alkyl) radical; a $C_1$–$C_6$ aminoalkyl radical; or a $C_1$–$C_6$ aminoalkyl radical whose amine is mono- or di-substituted by a $C_1$–$C_4$ alkyl, ($C_1$–$C_6$-alkyl)carbonyl, amido or ($C_1$–$C_6$-alkyl) sulfonyl radical;

$R_3$, $R_4$ and $R_5$ together, in pairs, with the nitrogen atom to which they are attached, form a saturated carbon ring containing 3 to 9 members, preferably 4, 5, 6, 7 or 8 members, which may contain one or more heteroatoms. As examples mention may be made of azetidine, pyrrolidine, piperidine, piperazine or morpholine rings, it being possible for said cationic heterocycle to be substituted by a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a $C_1$–$C_6$ alkoxy radical, a tri($C_1$–$C_6$-alkyl)silane($C_1$–$C_6$-alkyl) radical, an amido radical, a carboxyl radical, a ($C_1$–$C_6$-alkyl)carbonyl radical, a thio (—SH) radical, a $C_1$–$C_6$ thioalkyl (—R—SH) radical, a ($C_1$–$C_6$-alkyl)thio radical, an amino radical, or an amino radical mono- or di-substituted by a ($C_1$–$C_6$)alkyl, ($C_1$–$C_6$-alkyl)carbonyl, amido or ($C_1$–$C_6$-alkyl)sulfonyl radical;

Y" is a counterion.

In the formula (XIII), according to a more particular embodiment, $R_3$, $R_4$ and $R_5$ separately are selected preferably from a $C_1$–$C_6$ alkyl radical, a $C_1$–$C_4$ monohydroxyalkyl radical, a $C_2$–$C_4$ polyhydroxyalkyl radical, a ($C_1$–$C_6$-alkoxy)($C_1$–$C_4$-alkyl) radical, and a tri($C_1$–$C_6$-alkyl)silane ($C_1$–$C_6$-alkyl) radical, or $R_3$ together with $R_4$ form an azetidine ring, a pyrrolidine, piperidine, piperazine or morpholine ring, $R_5$ in this case being selected from a $C_1$–$C_6$ alkyl radical; a $C_1$–$C_6$ monohydroxyalkyl radical; and a $C_2$–$C_6$ polyhydroxyalkyl radical.

When the radical $R_2$ corresponds to the formula (XIII) it is preferably a trialkylammonium radical whose alkyl radicals may be substituted.

According to a second embodiment the radical $R_2$ represents the onium radical Z corresponding to the formula (XIV):

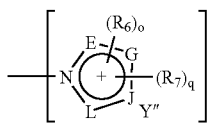

(XIV)

in which:
the ring members E, G, J and L, which are identical or different, represent a carbon, oxygen, sulfur or nitrogen atom, to form a pyrrole, pyrazole, imidazole, triazole, oxazole, isooxazole, thiazole or isothiazole ring;
q is an integer between 0 and 4 inclusive;
o is an integer between 0 and 3 inclusive;
q+o is an integer between 0 and 4 inclusive;
$R_7$, which are identical or different, represent a hydroxyl radical, a $C_1$–$C_6$ alkyl radical, a $C_1$–$C_6$ monohydroxyalkyl radical, a $C_2$–$C_6$ polyhydroxyalkyl radical, a $C_1$–$C_6$ alkoxy radical or a tri($C_1$–$C_6$-alkyl)silane ($C_1$–$C_6$-alkyl) radical; on the understanding that the radicals $R_7$ are borne by a carbon atom;
$R_6$, which is identical or different, represents a $C_1$–$C_6$ alkyl radical, a $C_1$–$C_6$ monohydroxyalkyl radical, a $C_2$–$C_6$ polyhydroxyalkyl radical, a tri($C_1$–$C_6$-alkyl)silane($C_1$–$C_6$-alkyl) radical, a ($C_1$–$C_6$-alkoxy)($C_1$–$C_6$-alkyl) radical, a carbamyl($C_1$–$C_6$-alkyl) radical, a ($C_1$–$C_6$-alkyl)carboxy($C_1$–$C_6$-alkyl) radical or a benzyl radical; on the understanding that the radicals $R_6$ are borne by a nitrogen; and
Y" is a counterion.

By way of example the ring members E, G, J and L may form a pyrrole, imidazole, pyrazole, oxazole, thiazole or triazole ring, preferably an imidazole ring.

According to a third embodiment $R_2$ represents the onium radical Z corresponding to the formula (XV):

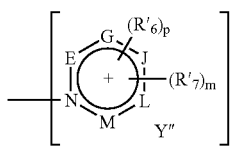

(XV)

in which:
the ring members E, G, J, L and M, which are identical or different, represent a carbon, oxygen, sulfur or nitrogen atom, to form a ring selected from pyridine, pyrimidine, pyrazine, triazine and pyridazine rings;
p is an integer between 0 and 3 inclusive;
m is an integer between 0 and 5 inclusive;
p+m is an integer between 0 and 5 inclusive;
$R'_7$, which are identical or different, represent a hydroxyl radical, a $C_1$–$C_6$ alkyl radical, a $C_1$–$C_6$ monohydroxyalkyl radical, a $C_2$–$C_6$ polyhydroxyalkyl radical, a $C_1$–$C_6$ alkoxy radical or a tri($C_1$–$C_6$-alkyl)silane ($C_1$–$C_6$-alkyl) radical; on the understanding that the radicals $R'_7$ are borne by a carbon atom;
$R'_6$, which is identical or different, represents a $c_1$–$C_6$ alkyl radical, a $C_1$–$C_6$ monohydroxyalkyl radical, a $C_2$–$C_6$ polyhydroxyalkyl radical, a tri($C_1$–$C_6$-alkyl)silane($C_1$–$C_6$-alkyl) radical, a ($C_1$–$C_6$-alkoxy)($C_1$–$C_6$-alkyl) radical, a carbamyl($C_1$–$C_6$-alkyl) radical, a ($C_1$–$C_6$-alkyl)carboxy($C_1$–$C_6$-alkyl) radical or a benzyl radical; on the understanding that the radicals $R'_6$ are borne by a nitrogen; and
Y" represents a counterion.

Preferably the ring members E, G, J, L and M form with the nitrogen of the ring a pyridine or pyrimidine ring.

Preferably $R_7$, $R_6$, $R'_7$ and $R'_6$ are alkyl radicals, which may be substituted.

In the context of the invention the counterion (Y") may be selected from a halogen atom such as bromine, chlorine, fluorine or iodine, a hydroxide, a citrate, a succinate, a tartrate, a lactate, a tosylate, a mesylate, a benzenesulfonate, an acetate, a hydrogen sulfate or a $C_1$–$C_6$ alkyl sulfate such as, for example, methyl sulfate or ethyl sulfate.

Preferably the counterion (Y") is selected from a halogen atom such as bromine, chlorine or iodine, a tosylate, a mesylate, a benzenesulfonate or a $C_1$–$C_6$ alkyl sulfate such as methyl sulfate or ethyl sulfate, for example.

Examples of compounds of the formula (I) which can be prepared by the process of the invention include the following:

| Nomenclature | Structures |
|---|---|
| [1-(4-Aminophenyl)-pyrrolidin-3-yl]-3-methyl-1H-imidazol-3-ium chloride, hydrochloride | 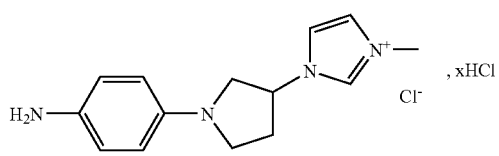 |
| [1-(4-Aminophenyl)-pyrrolidin-3-yl]trimethyl-ammonium chloride, hydrochloride | 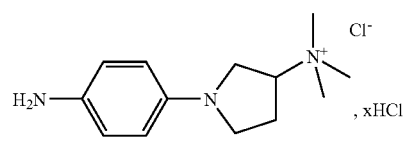 |

| Nomenclature | Structures |
|---|---|
| 1-(4-Aminophenyl)-pyrrolidine-3-amine dihydrochloride | 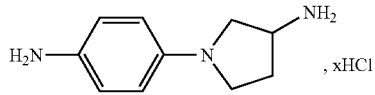, xHCl |
| 1-(4-Aminophenyl)-N,N-dihydroxyethylpyrrolidine-3-amine dihydrochloride | 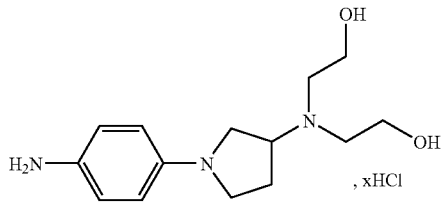, xHCl |
| [1-(4-Aminohenyl)-pyrrolidin-3-yl]pyridinium chloride, hydrochloride | 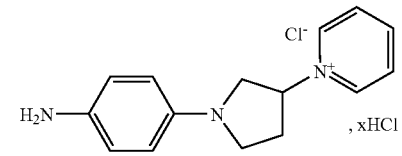, xHCl |
| [1-(4-Aminophenyl)-pyrrolidin-3-yl]methyl-piperidinium chloride, hydrochloride | 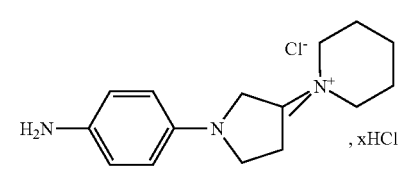, xHCl |
| 1-(4-Aminophenyl)-N-methylpyrrolidine-3-amine dihydrochloride | 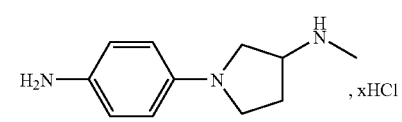, xHCl |
| 1-(4-Aminophenyl)-N,N-dimethylpyrrolidine-3-amine dihydrochloride | 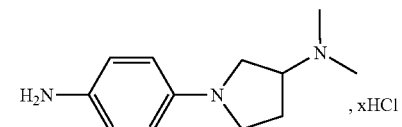, xHCl |
| 1-(4-Amino-3-methylphenyl)-pyrrolidine-3-amine dihydrochloride | 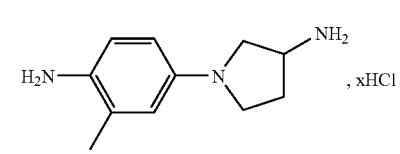, xHCl |
| [1-(4-Amino-3-methyl-phenyl)pyrrolidin-3-yl]-trimethylammonium chloride, hydrochloride | 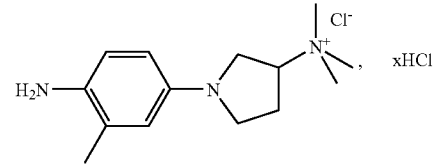, xHCl |
| [1-(4-Amino-3-methyl-phenyl)pyrrolidin-3-yl]-3-methyl-1H-imidazol-3-ium chloride, hydrochloride | 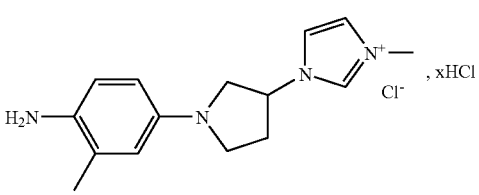, xHCl |

| Nomenclature | Structures |
|---|---|
| 1-(4-Amino-3-methylphenyl)-N,N-di-hydroxyethyl-pyr-rolidin-3-amine dihydrochloride | 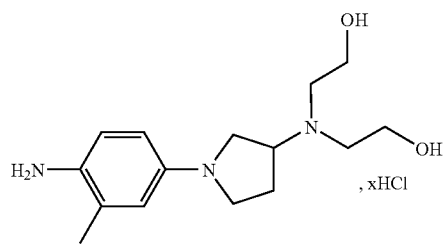 |
| 1-(4-Aminophenyl)-pyr-rolidine-3-amino-guanidine dihydrochloride | 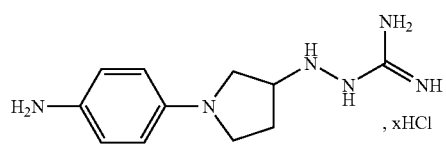 |

The various steps of the process of the invention are illustrated in scheme 5 below:

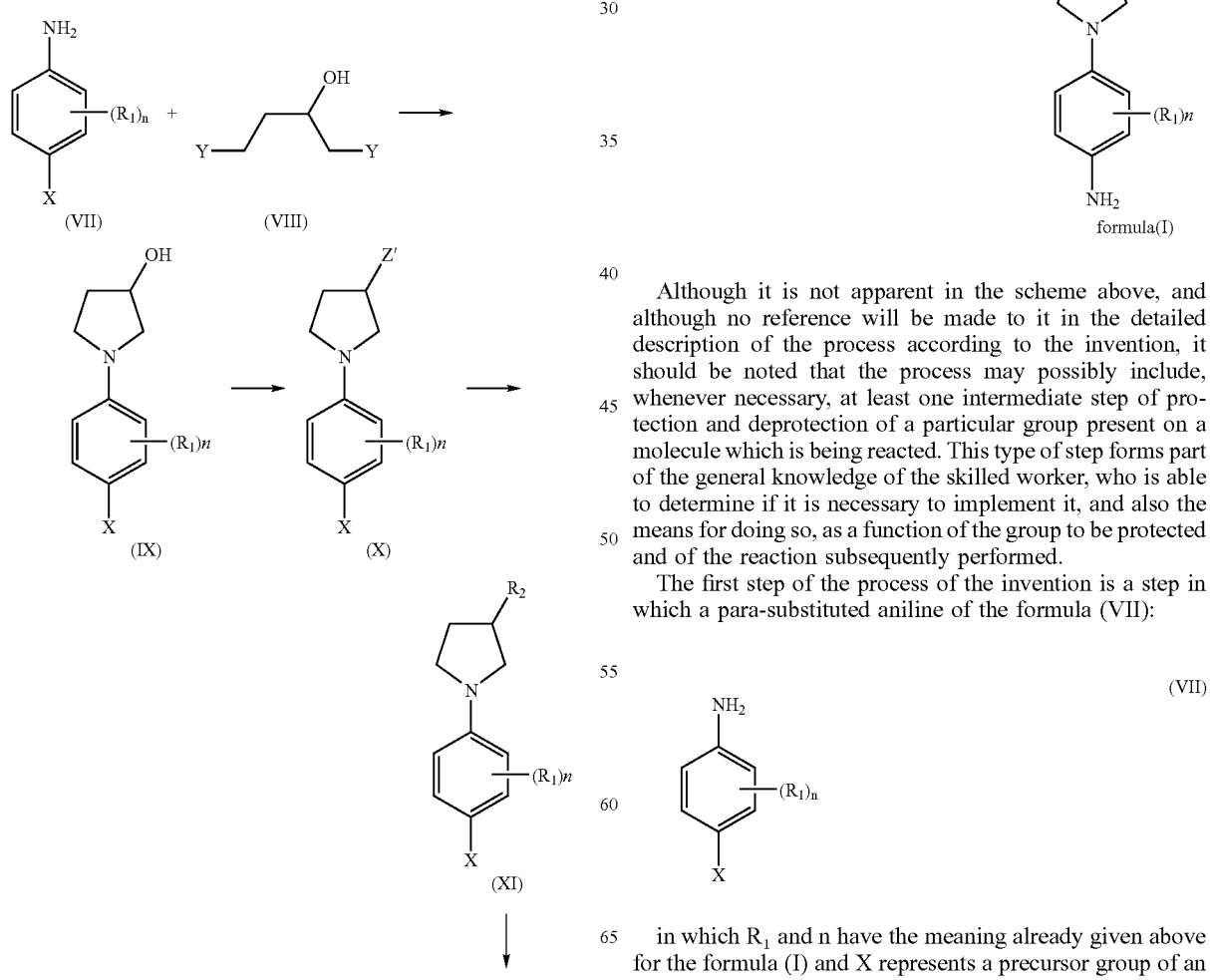

Although it is not apparent in the scheme above, and although no reference will be made to it in the detailed description of the process according to the invention, it should be noted that the process may possibly include, whenever necessary, at least one intermediate step of protection and deprotection of a particular group present on a molecule which is being reacted. This type of step forms part of the general knowledge of the skilled worker, who is able to determine if it is necessary to implement it, and also the means for doing so, as a function of the group to be protected and of the reaction subsequently performed.

The first step of the process of the invention is a step in which a para-substituted aniline of the formula (VII):

in which $R_1$ and n have the meaning already given above for the formula (I) and X represents a precursor group of an amine function—as examples of groups of this type mention may be made in particular of nitro, —NHCOR and —NH-COOR groups, where R represent a saturated or unsaturated, preferably saturated, linear or branched $C_1$ to $C_6$ aliphatic chain, an aryl group or an arylalkyl group whose alkyl moiety is $C_1$–$C_6$— is condensed with a derivative of formula (VIII):

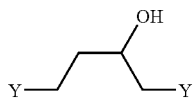

(VIII)

in which Y represents a leaving group, to give a compound of the formula (IX):

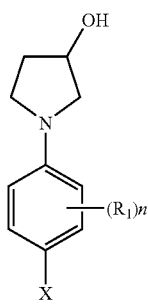

(IX)

in which $R_1$, X and n have the meanings (and the preferred meanings) already given above.

By leaving group is meant, conventionally, any radical capable of being removed in the course of a chemical reaction. In the present case, and by way of examples, this group is more particularly selected from a halogen, such as Cl, Br or I; a radical —$OSO_2R'$ or —$OSO_3R'$, where R' represents a saturated or unsaturated, linear or branched $C_1$–$C_6$ aliphatic radical, an aryl radical or an arylalkyl radical whose alkyl moiety is $C_1$–$C_6$. Preferably R' represents a methyl, para-methylphenyl, ethyl, phenyl or benzyl radical.

Preferred compounds of formula (VIII) are selected from dibromobutanol, ditosylbutanol and dimesylbutanol. Preferred compounds of the formula (VII) are selected from para-acetamidoaniline and para-acetamido-meta-methylaniline.

The condensation of the para-substituted aniline of the formula (VII) with the compounds of the formula (VIII) is carried out in a way which is known to the skilled worker. By way of example it is possible to follow a procedure of heating the mixture of the aniline (VII) and the compound of the formula (VII) at between 30° and 150° C. for 1 hour to 24 hours in a solvent, preferably such as ethanol, dimethylformamide, isopropanol, toluene, tetrahydrofuran, methyl tert-butyl ether or isopropyl acetate. Conventionally this reaction is performed in the presence of a base such as, for example, $CH_3COONa$, $Na_2CO_3$ or $K_2CO_3$.

The compound (IX), which is generally in solid form following treatment of the reaction mixture with water, is separated, by filtration for example, and used for the second step b) of the process according to the invention.

In the following step b) the compound of formula (IX) above is activated, to give a compound of the formula (X):

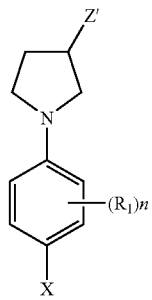

(X)

in which X, $R_1$ and n have the meaning (and the preferred meanings) already given above and Z' represents a leaving group. The definition indicated above for Y remains valid in the case of Z', and reference may be made thereto.

The reaction of activating the compound of the formula (IX) may be carried out, for example, by treatment with a sulfonyl halide in pyridine. It is likewise possible to contemplate employing an inert solvent, such as in particular dichloromethane, 1,2-dichloroethane, toluene, tetrahydrofuran or ethyl acetate, in the presence of an organic or inorganic base of the triethylamine or sodium carbonate type. The preferred activating reagent is methanesulfonyl chloride or toluenesulfonyl chloride, which gives a group Z' which is an $MeSO_3$— group or $C_7H_7SO_3$— group on the pyrrolidinyl ring.

The compound (X), which is generally present in solid form, is separated from the reaction mixture, by filtration for example, following treatment with water and is used for the third step c) of the process of the invention.

In the following step c) the compound of formula (X) is reacted with ammonia or with a primary, secondary or tertiary amine, or else with a compound bearing an aromatic nitrogen-containing heterocycle, to give a compound of the formula (XI):

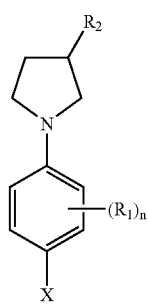

(XI)

in which X, $R_1$, $R_2$ and n have the meaning (and the preferred meanings) already given above.

As far as the primary, secondary or tertiary amine is concerned use may be made of a compound of the following formula:

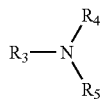

in which:

$R_3$, $R_4$ and $R_5$, taken separately, which are identical or different, represent a hydrogen atom, a saturated or unsaturated, linear or branched, $C_1$–$C_{22}$, aliphatic radical, preferably a $C_1$–$C_{22}$ alkyl radical; a saturated or unsaturated, $C_3$–$C_8$, alicyclic radical; a $C_1$–$C_{22}$, preferably $C_1$–$C_6$, monohydroxyalkyl radical; a $C_2$–$C_{22}$, preferably $C_2$–$C_6$ polyhydroxyalkyl radical; a ($C_1$–$C_6$-alkoxy)($C_1$–$C_{22}$, preferably $C_1$–$C_6$-alkyl) radical; an aryl radical; an arylalkyl radical whose alkyl moiety is $C_1$–$C_6$, such as the benzyl radical, for example; an amido($C_1$–$C_6$-alkyl) radical; a tri($C_1$–$C_6$-alkyl)silane($C_1$–$C_6$-alkyl) radical; a $C_1$–$C_6$ aminoalkyl radical; or a $C_1$–$C_6$ aminoalkyl radical whose amine is mono- or di-substituted by a $C_1$–$C_4$ alkyl, ($C_1$–$C_6$-alkyl)carbonyl, amido or ($C_1$–$C_6$-alkyl)sulfonyl radical; or $R_3$, $R_4$ and $R_5$ together, in pairs, with the nitrogen atom to which they are attached, form a saturated carbon ring containing 3 to 9 members, preferably 4, 5, 6, 7 or 8 members, which may contain one or more heteroatoms. As examples mention may be made of azetidine, pyrrolidine, piperidine, piperazine or morpholine rings, it being possible for said cationic heterocycle to be substituted by a halogen atom, an hydroxyl radical, a $C_1$–$C_6$ alkyl radical, a $C_1$–$C_6$ monohydroxyalkyl radical, a $C_2$–$C_6$ polyhydroxyalkyl radical, a $C_1$–$C_6$ alkoxy radical, a tri($C_1$–$C_6$-alkyl)silane($C_1$–$C_6$-alkyl) radical, an amido radical, a carboxyl radical, a ($C_1$–$C_6$-alkyl)carbonyl radical, a thio (—SH) radical, a $C_1$–$C_6$ thioalkyl (—R—SH) radical, a ($C_1$–$C_6$-alkyl)thio radical, an amino radical, or an amino radical mono- or di-substituted by a ($C_1$–$C_6$)alkyl, ($C_1$–$C_6$-alkyl) carbonyl, amido or ($C_1$–$C_6$-alkyl)sulfonyl radical.

It is likewise possible to contemplate implementing the step with aminoguanidine ($H_2N$—NH—C($NH_2$)=NH).

As far as the compound containing at least one aromatic nitrogen-containing heterocycle is concerned mention may be made of the compounds of the following formula:

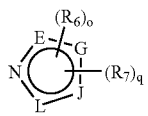

in which:
the ring members E, G, J and L, which are identical or different, represent a carbon, oxygen, sulfur or nitrogen atom, to form a pyrrole, pyrazole, imidazole, triazole, oxazole, isooxazole, thiazole or isothiazole ring;
q is an integer between 0 and 4 inclusive;
o is an integer between 0 and 3 inclusive;
q+o is an integer between 0 and 4 inclusive;
$R_7$, which are identical or different, represent a hydroxyl radical, a $C_1$–$C_6$ alkyl radical, a $C_1$–$C_6$ monohydroxyalkyl radical, a $C_2$–$C_6$ polyhydroxyalkyl radical, a $C_1$–$C_6$ alkoxy radical or a tri($C_1$–$C_6$-alkyl)silane($C_1$–$C_6$-alkyl) radical; on the understanding that the radicals $R_7$ are borne by a carbon atom;
$R_6$, which is identical or different, represents a $C_1$–$C_6$ alkyl radical, a $C_1$–$C_6$ monohydroxyalkyl radical, a $C_2$–$C_6$ polyhydroxyalkyl radical, a tri($C_1$–$C_6$-alkyl)silane($C_1$–$C_6$-alkyl) radical, or a benzyl radical; on the understanding that the radicals $R_6$ are borne by a nitrogen.

By way of example the ring members E, G, J and L may form a pyrrole, imidazole, pyrazole, oxazole, thiazole and triazole ring, preferably an imidazole ring.

It is also possible to use a compound of the following formula:

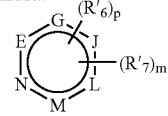

in which:
the ring members E, G, J, L and M, which are identical or different, represent a carbon, oxygen, sulfur or nitrogen atom, to form a ring selected from pyridine, pyrimidine, pyrazine, triazine and pyridazine rings;
p is an integer between 0 and 3 inclusive;
m is an integer between 0 and 5 inclusive;
p+m is an integer between 0 and 5 inclusive;
$R'_7$, which are identical or different, represent a hydroxyl radical, a $C_1$–$C_6$ alkyl radical, a $C_1$–$C_6$ monohydroxyalkyl radical, a $C_2$–$C_6$ polyhydroxyalkyl radical, a $C_1$–$C_6$ alkoxy radical or a tri($C_1$–$C_6$-alkyl)silane ($C_1$–$C_6$-alkyl) radical; on the understanding that the radicals $R'_7$ are borne by a carbon atom;
$R'_6$, which is identical or different, represents a $C_1$–$C_6$ alkyl radical, a $C_1$–$C_6$ monohydroxyalkyl radical, a $C_2$–$C_6$ polyhydroxyalkyl radical, a tri($C_1$–$C_6$-alkyl)silane($C_1$–$C_6$-alkyl) radical, a ($C_1$–$C_6$-alkoxy)($C_1$–$C_6$-alkyl) radical, a carbamyl($C_1$–$C_6$-alkyl) radical, a ($C_1$–$C_6$-alkyl)carboxy($C_1$–$C_6$-alkyl) radical or a benzyl radical; on the understanding that the radicals $R'_6$ are borne by a nitrogen.

Preferably the ring members E, G, J, L and M form, with the nitrogen of the ring, a pyridine and pyrimidine ring.

According to one advantageous embodiment of the invention the primary amines are selected from methylamine, ethylamine, propylamine, butylamine, isopropylamine, aniline and benzylamine.

As far as the secondary amines are concerned they are preferably selected from dimethylamine, diethylamine, methylethylamine, diisopropylamine, dihydroxyethylamine and pyrolidine.

As far as the tertiary amines are concerned they are advantageously selected from trimethylamine, triethylamine, dimethylethylamine and N-methyl-piperidine.

As for the compounds bearing an aromatic nitrogen-containing heterocycle they are preferably selected from imidazole, N-methylimidazole and pyridine.

In this step c) the reaction of the compound of the formula (X) with an amine or a compound bearing an aromatic heterocycle is carried out in a manner known per se. More particularly, by way of example, the reaction may be performed by heating at between 50° C. and 150° C. for 1 hour to 24 hours, in a solvent such as methyl isobutyl ketone, methyl ethyl ketone, tetrahydrofuran, isobutanol, propanol, tert-butyl-methyl ether, isopropyl acetate or toluene, in particular.

The products obtained in step c) of the process of the invention are generally solid products which can be separated from the reaction mixture, by filtration for example, before being used in step d) of the process of the invention.

In step d) the group X is transformed into an amine function, to give the desired end compound of the formula (I).

More particularly the compound of the formula (XI) is hydrolyzed when X represents an —NHCOR or —NHCOOR group, as defined earlier.

According to another possibility a reduction reaction, such as hydrogenation, is performed on the compound of the formula (XI), when X represents a nitro group.

As a non-limitative implementation example the hydrolysis reaction on the compound of the formula (XI) is carried out in a solvent such as, in particular, water, ethanol or isopropanol in the presence of an inorganic acid such as, for example, hydrochloric acid, hydrobromic acid or sulfuric acid. Conventionally the reaction temperature is between 20° C. and 120° C.

The hydrogenation reaction on the compound of the formula (XI) is generally carried out in a solvent such as methanol, ethanol or isopropanol, advantageously in the presence of a catalyst of the palladium-on-carbon type, under a hydrogen pressure of between 1 and 50 bars and at a temperature of 20° C. to 120° C.

The invention additionally relates to some of the intermediates of the formula (IX), which are new compounds.

These are compounds of the formula (IX) defined above in the context of the description of the process, but with the exclusion of certain specific compounds.

These new intermediate compounds correspond to the formula:

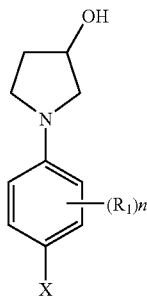

(IX)

in which:
  the carbon bearing the hydroxyl substituent on the pyrrolidine ring is racemic or chiral;
  n is an integer from 0 to 4, on the understanding that, when n is greater than or equal to 2, the radicals $R_1$ can be identical or different;
  $R_1$ represents a halogen atom; a saturated or unsaturated, $C_3$–$C_8$ alicyclic, or $C_1$–$C_6$ aliphatic, hydrocarbon chain, an aryl radical, an arylalkyl radical whose alkyl moiety is $C_1$–$C_6$, it being possible for one or more carbon atoms of the hydrocarbon chain and of the alkyl chain of the arylalkyl radical to be replaced by an oxygen, nitrogen, silicon or sulfur atom or by an $SO_2$ group; the radical $R_1$ not containing a peroxide linkage, nor diazo, nitro or nitroso radicals;
  X represents a group —NHCOR or —NHCOOR, a nitroso group or a nitro group, where R represent a saturated or unsaturated, preferably saturated, linear or branched, $C_1$–$C_6$, aliphatic chain, an aryl group or an arylalkyl group whose alkyl moiety is $C_1$–$C_6$, with the exception of the three compounds in the table below:

| | |
|---|---|
| (R)-[1-(4-nitro-3-methoxyphenyl)pyrrolidin-3-ol] | 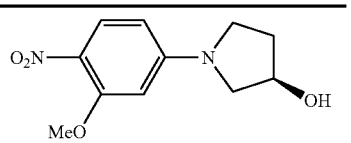 |
| (R)-[1-(4-nitro-2-fluorophenyl)pyrrolidin-3-ol] | 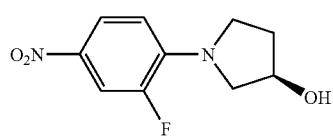 |
| (R)-[1-(4-nitrophenyl)-pyrrolidin-3-ol] | 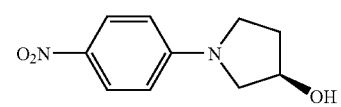 | and with the exception of the following compounds:

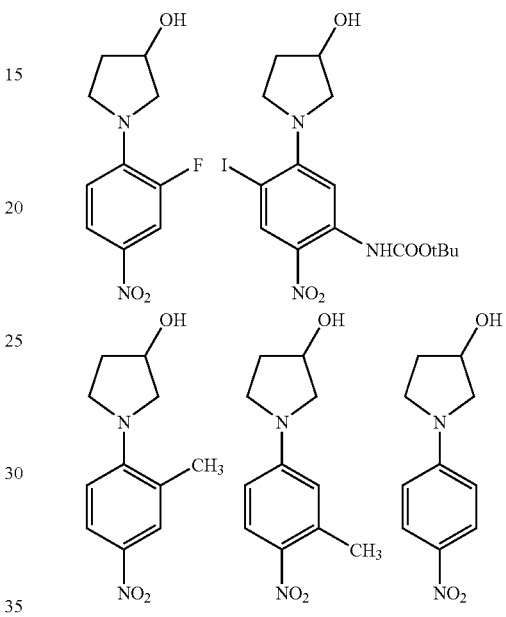

The invention relates, finally, to some of the compounds of the formula (XI), which are new compounds.

These are compounds of the formula (XI), defined above in the context of the process, but with the exclusion of certain specific compounds and of the compounds where $X=NO_2$.

These new compounds correspond to the formula (XI):

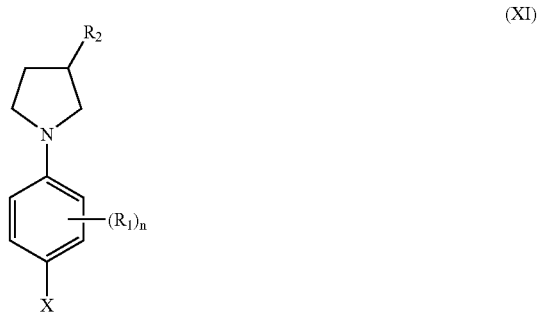

(XI)

in which:
  the carbon bearing the substituent $R_2$ on the pyrrolidine ring is racemic or chiral; $R_1$, n and X have the same meanings as in the formula (IX) above, except that X does not represent a nitro group; and $R_2$ represents a cationic or noncationic nitrogenous radical; with the exception of the compound of the following formula:

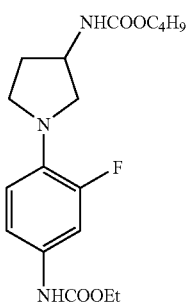

Reference may be made to what was indicated earlier concerning these compounds, especially the preferred definitions of the radicals, and their preparation.

The invention will now be described with reference to the following examples, which are given by way of illustration and not of limitation.

EXAMPLES

In Examples 1 to 3 below the compounds (1), (2) and (3) are prepared for the process according to the invention.

Example 1

Synthesis of [1-(4-aminophenyl)pyrrolidin-3-yl] trimethylammonium chloride, hydrochloride (compound 1)

Compound 1 is prepared according to the following scheme:

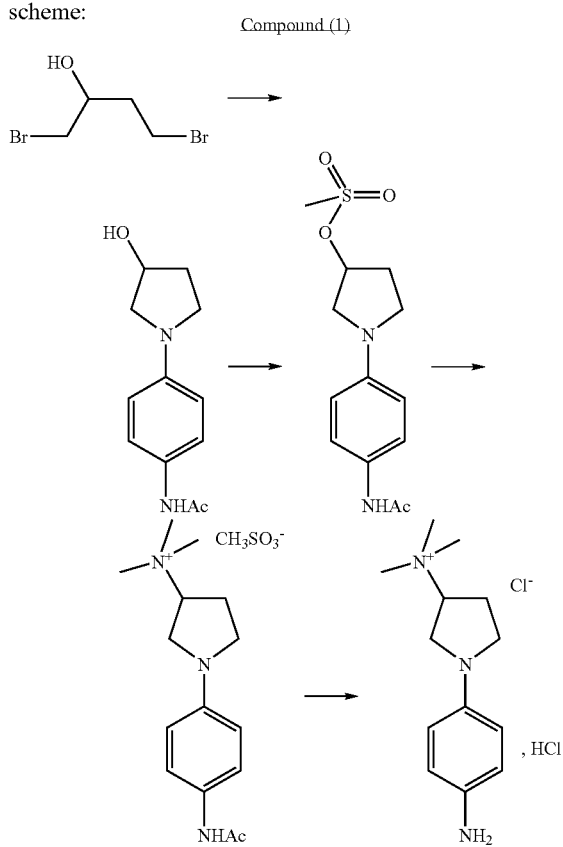

Step 1

N-[4-(3-hydroxypyrrolidin-1-yl)phenyl]-acetamide

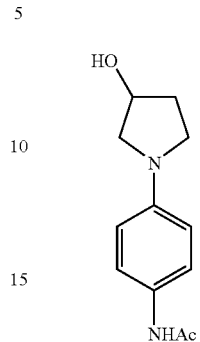

A reactor is charged under a nitrogen atmosphere with 65 g (0.433 mol) of 4-aminoacetanilide and 68.8 g (0.649 mol) of $Na_2CO_3$ in 260 ml of isopropanol.

This initial charge is heated to reflux and then 130.9 g of 1,4-dibromo-2-butanol are added dropwise. The mixture is heated at reflux for 4 h and then cooled to 20° C.

260 ml of water are added and the precipitate is filtered off, washed with water and then dried under vacuum at 40° C. This gives 69.3 g of a beige solid, corresponding to a final yield of 72.7%.

Analyses

The mass spectrum and the 1H and 13C NMR spectra are in accordance with the anticipated structure.

Melting point (DSC): 175.5° C. Elemental analysis (C12H16N2O2; MW=220.27)

|  | C | H | N | O |
| --- | --- | --- | --- | --- |
| % theoretical | 65.44 | 7.32 | 12.72 | 14.53 |
| % found | 65.43 | 7.37 | 12.85 | 14.78 |

Step 2

1-(4-Acetylaminophenyl)pyrrolidin-3-yl ester of methanesulfonic acid

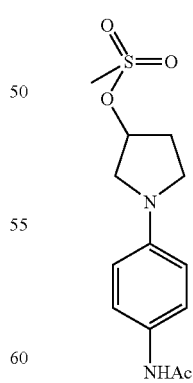

A reactor is charged under a nitrogen atmosphere with 50 g (0.227 mol) of the compound from step 1 in 250 ml of pyridine. This initial charge is cooled to 0° C. and then 21.2 ml (0.272 mol) of methanesulfonyl chloride are added, during which the temperature is held at below 5° C. The mixture is stirred at 5° C. for 3 h and then poured into 750 ml of water. The system is filtered and the solid is rinsed with water and then dried under vacuum at 40° C. This gives 58 g of a pinky-beige solid, corresponding to a final yield of 83%.

Analyses

The mass spectrum and the 1H and 13C NMR spectra are in accordance with the anticipated structure.

Melting point (DSC): 150–155° C. Elemental analysis (C13H18N2O4S; MW=298.36)

|  | C | H | N | O | S |
|---|---|---|---|---|---|
| % theoretical | 52.33 | 6.08 | 9.39 | 21.45 | 10.75 |
| % found | 52.21 | 6.08 | 9.36 | 21.50 | 10.62 |

Step 3

3-[1-(4-acetylaminophenyl)pyrrolidin-3-yl]-trimethylammonium methanesulfonate

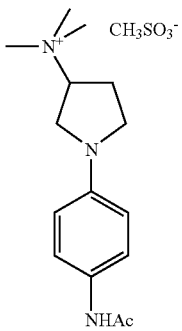

An autoclave is charged with 2 g (6.7 mmol) of the compound from step 2 in 20 ml of a solution of trimethylamine in ethanol (4.2M). The mixture is heated at 120° C. for 4 h and then cooled to 20° C. The mixture is poured onto 50 ml of acetone and the precipitate is filtered off and dried under vacuum. This gives 1.4 g of crude product, which is recrystallized from isopropanol to give 1.25 g of a pale beige solid, corresponding to a final yield of 52%.

Analyses

The mass spectrum and the 1H and 13C NMR spectra are in accordance with the anticipated structure.

Step 4

[1-(4-Aminophenyl)pyrrolidin-3-yl]trimethyl-ammonium chloride, hydrochloride (compound (1))

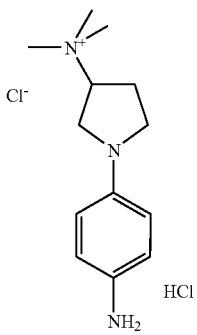

A reactor is charged with 1 g of the derivative from step 3, N-acetylated in 5 ml of ethanol and 1.2 ml of concentrated HCl (35% aq.). This initial charge is heated at reflux for 4 h and cooled to 20° C. The mixture is filtered and the precipitate is washed with isopropanol and dried under vacuum over potassium hydroxide. This gives 0.30 g of a white solid, corresponding to a final yield of 36.5%.

Analyses

The mass spectrum and the 1H and 13C NMR spectra are in accordance with the anticipated structure.

Example 2

[1-(4-Aminophenyl)pyrrolidin-3-yl]-1-methyl-3H-imidazol-1-ium chloride, hydrochloride (compound (2))

Compound (2) is prepared according to the following scheme:

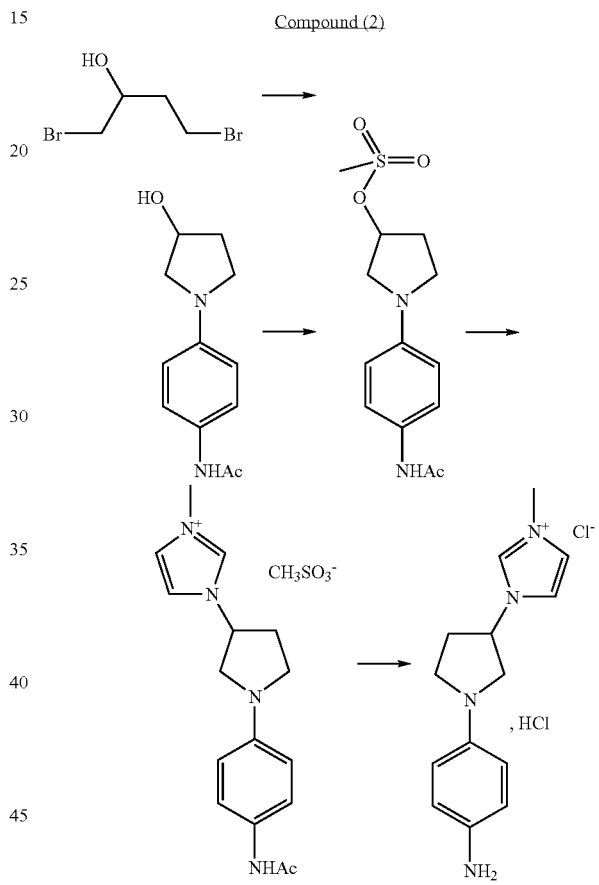

Step 1

This step is similar to step 1 of Example 1, in which the following compound is prepared:

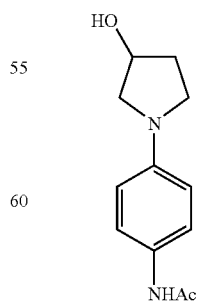

Step 2

This step is similar to step 2 of Example 1, in which the following compound is prepared:

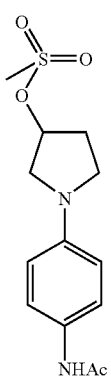

Step 3

3-[1-4-Acetylaminophenyl)pyrrolidin-3-yl]-1-methyl-3H-imidazol-1-ium methanesulfonate

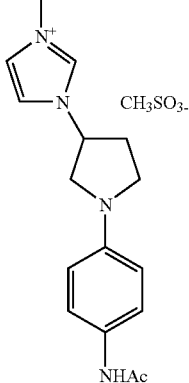

A reactor is charged under a nitrogen atmosphere with 37.5 g (0.1257 mol) of the preceding compound from step 2 in 300 ml of methyl isobutyl ketone. The mixture is heated to 80° C. and then 40 ml of N-methylimidazole are added dropwise. The mixture is subsequently heated at reflux at 120° C. for 4 h, cooled to 20° C. and then filtered. The solid is washed with acetone and then dried under vacuum. This gives 38 g of a pale beige solid, corresponding to a yield of 80%.

Analyses

The mass spectrum and the 1H and 13C NMR spectra are in accordance with the anticipated structure.

Step 4

[1-(4-Aminophenyl)pyrrolidin-3-yl]-1-methyl-3H-imidazol-1-ium chloride, hydrochloride (compound (2))

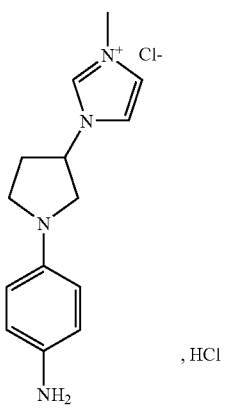

A reactor is charged with 10 g of the N-acetylated derivative of Example 3 in 50 ml of ethanol and 11 ml of concentrated HCl (37% aq.). The mixture is heated at reflux for 1 h and then the water is removed by azeotropic distillation. The remaining product is cooled to 20° C. and filtered and the precipitate is washed with ethanol and dried under vacuum over potassium hydroxide. This gives 7.5 g of a pale beige solid, corresponding to a final yield of 91%.

Analyses

The mass spectrum and the 1H and 13C NMR spectra are in accordance with the anticipated structure.

Melting point (DSC): 287.2° C. Elemental analysis (C14H19N4Cl ClH; MW=315.25)

|              | C     | H    | N     | Cl    |
|--------------|-------|------|-------|-------|
| % theoretical | 53.34 | 6.39 | 17.77 | 22.49 |
| % found       | 52.87 | 6.34 | 17.80 | 22.66 |

Example 3

1-(4-Aminophenyl)-N,N-dimethylpyrrolidine-3-amine dihydrochloride, (compound (3))

Compound (3) is prepared according to the following scheme:

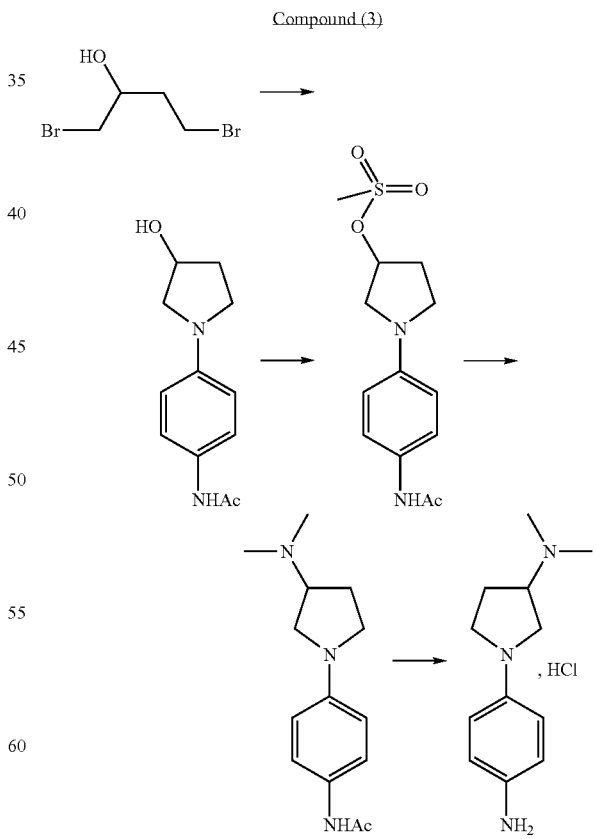

Steps 1 and 2

These steps are in common with Examples 1 and 2.

Step 3

N-[4-(3-dimethylaminopyrrolidin-1-yl)phenyl]-acetamide

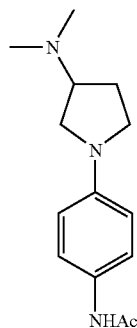

This step is carried out under the same conditions as in Example 1 and Example 2, using as amine-containing group dimethylamine in solution in ethanol. This gives 1.2 g of a beige solid, corresponding to a final yield of 70%.

Analyses

The mass spectrum and the 1H and 13C NMR spectra are in accordance with the anticipated structure.

Step 4

1-(4-Aminophenyl)-N,N-dimethylpyrrolidine-3-amine dihydrochloride (compound 3)

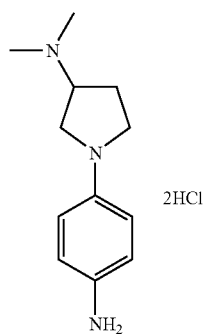

In accordance with the same operating conditions as Examples 1 and 2, starting from the N-acetylated compound previously described in step 3, the desired compound is obtained with a final yield of 80%.

Analyses

The mass spectrum and the 1H and 13C NMR spectra are in accordance with the anticipated structure.

Elemental analysis (C12H19N3, 2HCl; MW=278.227)

|  | C | H | N | Cl |
|---|---|---|---|---|
| % theoretical | 51.8 | 7.61 | 15.1 | 25.48 |
| % found | 51.23 | 7.73 | 14.83 | 25.46 |

The invention claimed is:

1. A process for synthesizing a para-phenylenediamine derivative compound comprising a pyrolidinyl group and substituted by a nitrogenous radical, wherein the para-phenylenediamine derivative compound is chosen from those of formula (I):

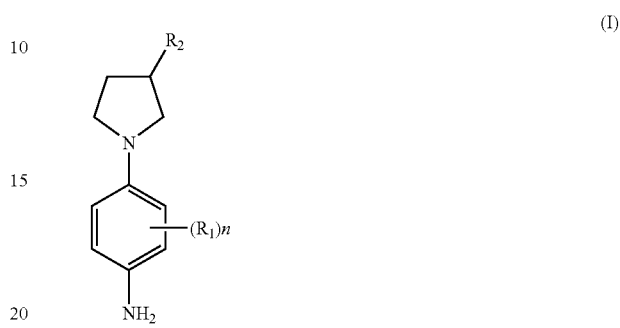

(I)

wherein:

the carbon with the substituent $R_2$ on the pyrrolidine ring may be in either (R) or (S) configuration, n is an integer ranging from 0 to 4, such that, when n is greater than or equal to 2, the radicals $R_1$ may be identical or different;

$R_1$ is chosen from halogen atoms; saturated and unsaturated, $C_3$–$C_8$ alicyclic, and $C_1$–$C_6$ linear and branched aliphatic, hydrocarbon chains; aryl radicals; and arylalkyl radicals wherein the alkyl chain is chosen from $C_1$–$C_6$ alkyl chains, it being possible for at least one carbon atom of the hydrocarbon chain and of the alkyl chain of the arylalkyl radical to be replaced by an entity chosen from oxygen, nitrogen, silicon and sulfur atoms and by $SO_2$ groups; with the proviso that the radical $R_1$ does not contain a peroxide linkage, nor diazo, nitro or nitroso radicals; and $R_2$ is chosen from cationic and noncationic nitrogenous radicals;

comprising the following successive steps:

a) a para-substituted aniline of the formula (VII):

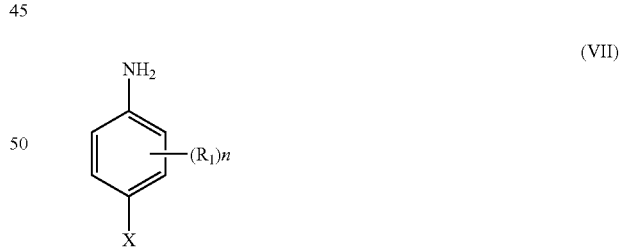

(VII)

wherein $R_1$ and n are as defined above for formula (I), and X is a precursor group of an amine functional group, is condensed with a derivative of formula (VIII):

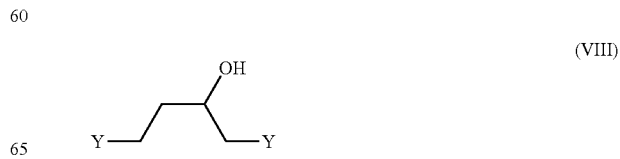

(VIII)

wherein Y is a leaving group, to give a compound of the formula (IX):

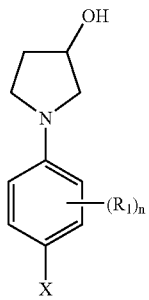

wherein X, $R_1$ and n are as defined above;
b) the compound of formula (IX) is activated, to give a compound of formula (X):

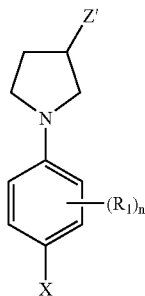

wherein X, $R_1$ and n are as defined above and Z' is a leaving group;
c) the compound of formula (X) is reacted with a group chosen from:
ammonia; a primary, secondary and tertiary amine; or a compound bearing a nitrogen-containing aromatic heterocycle; to give a compound of formula (XI):

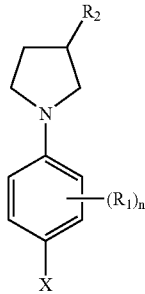

wherein X, $R_1$, $R_2$ and n are as defined above; and
d) the group X is converted to an amine functional group, to give the compound of formula (I).
2. The process as claimed in claim 1, wherein n is 0.
3. The process as claimed in claim 1, wherein
n is other than zero, and
$R_1$ is chosen from halogen atoms; saturated and unsaturated, $C_3$–$C_8$ alicyclic, and $C_1$–$C_6$ aliphatic, hydrocarbon chains, aryl radicals, arylalkyl radicals whose alkyl chain is $C_1$–$C_6$, it being possible for one or more carbon atoms of the hydrocarbon chain and of the alkyl chain of the arylalkyl radical to be replaced by an oxygen, nitrogen, silicon or sulfur atom or by an $SO_2$ group; the radical $R_1$ not containing a peroxide linkage, nor diazo, nitro or nitroso radicals.
4. The process as claimed in claim 3, wherein n is 1.
5. The process as claimed in claim 1, wherein $R_1$ is chosen from chlorine and bromine atoms, and $C_1$–$C_4$ alkyl radicals, $C_1$–$C_4$ hydroxyalkyl radicals, $C_1$–$C_4$ aminoalkyl radicals, $C_1$–$C_4$ alkoxy radicals, and $C_1$–$C_4$ hydroxyalkoxy radicals.
6. The process as claimed in claim 5, wherein $R_1$ is chosen from methyl hydroxymethyl, 2-hydroxyethyl, 1,2-dihydroxyethyl, methoxy, isopropyloxy and 2-hydroxyethoxy radicals.
7. The process as claimed in claim 1, wherein, in formula (I), $R_2$ is a noncationic nitrogenous radical chosen from primary (—$NH_2$), secondary (—NHR) and tertiary (—N$(R)_2$) amine radicals
wherein R, which may be identical or different, are chosen from saturated and unsaturated, linear and branched $C_1$–$C_{22}$ aliphatic radicals;
saturated and unsaturated $C_3$–$C_8$ alicyclic radicals;
$C_1$–$C_{22}$ monohydroxyalkyl radicals;
$C_2$–$C_{22}$ polyhydroxyalkyl radicals;
$C_1$–$C_6$-alkoxy radicals;
$C_2$–$C_{22}$-alkyl radicals;
aryl radicals;
$C_1$–$C_6$ arylalkyl radicals;
amido($C_1$–$C_6$-alkyl) radicals;
tri($C_1$–$C_6$-alkyl)silane($C_1$–$C_6$-alkyl) radicals;
$C_1$–$C_6$ aminoalkyl radicals; and
$C_1$–$C_6$ aminoalkyl radicals whose amine is mono- or di-substituted by a group chosen from $C_1$–$C_4$ alkyl, ($C_1$–$C_6$-alkyl)carbonyl, amido and ($C_1$–$C_6$-alkyl)sulfonyl radicals;
wherein radicals optionally form, in pairs, together with the nitrogen atom to which they are attached, a saturated carbon ring comprising 3 to 9 members, optionally comprising at least heteroatom, said heterocycle optionally substituted by at least one substituent chosen from halogen atoms, hydroxyl radicals, $C_1$–$C_6$ alkyl radicals, $C_1$–$C_6$ monohydroxyalkyl radicals, $C_2$–$C_6$polyhydroxyalkyl radicals, $C_1$–$C_6$alkoxy radicals, tri($C_1$–$C_6$-alkyl)silane($C_1$–$C_6$-alkyl) radicals, amido radicals, carboxyl radicals, ($C_1$–$C_6$-alkyl)carbonyl radicals, thio (—SH) radicals, $C_1$–$C_6$ thioalkyl (—R—SH) radicals, ($C_1$–$C_6$-alkyl)thio radicals, amino radicals, and amino radicals mono- or di-substituted by at least one radical chosen from ($C_1$–$C_6$)alkyl, ($C_1$–$C_6$-alkyl)carbonyl, amido and ($C_1$–$C_6$-alkyl)sulfonyl radicals.
8. The process as claimed in claim 1, wherein, in formula (I), $R_2$ is a noncationic nitrogenous radical derived from aminoguanidine.
9. The process as claimed in claim 1, wherein in formula (I) $R_2$ is an onium radical of formula (XIII):

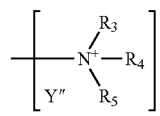

wherein:
R₃, R₄ and R₅, which may be identical or different, are chosen from hydrogen atoms, saturated and unsaturated, linear and branched $C_1$–$C_{22}$ aliphatic radicals; saturated and unsaturated $C_3$-$C_8$ alicyclic radicals; $C_1$–$C_{22}$, monohydroxyalkyl radicals; $C_2$–$C_{22}$ polyhydroxyalkyl radicals; ($C_1$–$C_6$-alkoxy)($C_1$–$C_{22}$ alkyl) radicals; aryl radicals; arylalkyl radicals whose alkyl moiety is $C_1$–$C_6$; tri($C_1$–$C_6$-alkyl)silane($C_1$–$C_6$-alkyl) radicals; $C_1$–$C_6$ aminoalkyl radicals; $C_1$–$C_6$ aminoalkyl radicals whose amine is mono- or di-substituted by one or two groups chosen from $C_1$–$C_4$ alkyl, ($C_1$–$C_6$-alkyl) carbonyl, amido and ($C_1$–$C_6$-alkyl)sulfonyl radicals;

R₃, R₄ and R₅, in pairs, with the nitrogen atom to which they are attached, form a saturated carbon ring comprising 3 to 9 members, optionally comprising at least one heteroatom, said ring optionally substituted by at least one substituent chosen from halogen atoms, hydroxyl radicals, $C_1$–$C_6$ alkyl radicals, $C_1$–$C_6$ monohydroxyalkyl radicals, $C_2$–$C_6$ polyhydroxyalkyl radicals, $C_1$–$C_6$ alkoxy radicals, tri($C_1$–$C_6$-alkyl)silane ($C_1$–$C_6$ alkyl) radicals, amido radicals, carboxyl radicals, ($C_1$–$C_6$-alkyl)-carbonyl radicals, thio (—SH) radicals, $C_1$–$C_6$ thioalkyl (—R—SH) radicals, ($C_1$–$C_6$-alkyl)thio radicals, amino radicals, and amino radicals mono- or di-substituted by one or two groups chosen from ($C_1$–$C_6$)alkyl, ($C_1$–$C_6$-alkyl)carbonyl, amido and ($C_1$–$C_6$-alkyl)sulfonyl radicals; and Y″ is a counterion.

10. The process as claimed in claim 9, wherein R₃, R₄ and R₅, independently from each other, are chosen from $C_1$–$C_6$ alkyl radicals, $C_1$–$C_4$ monohydroxyalkyl radicals, $C_2$–$C_4$ polyhydroxyalkyl radicals, ($C_1$–$C_6$-alkoxy)($C_1$–$C_4$-alkyl) radicals, and tri($C_1$–$C_6$-alkyl)silane($C_1$–$C_6$-alkyl) radicals.

11. The process as claimed in claim 9, wherein R₃ together with R₄ form an azetidine, pyrrolidine, piperidine, piperazine or morpholine ring, and wherein R₅ is chosen from $C_1$–$C_6$ alkyl radicals; $C_1$–$C_6$ monohydroxyalkyl radicals; and $C_2$–$C_6$ polyhydroxyalkyl radicals.

12. The process as claimed in claim 10, wherein in formula (I), R₂ is a trialkylammonium optionally substituted with at least one alkyl radical.

13. The process as claimed in claim 1, wherein in formula (I), R₂ is an onium radical of formula (XIV):

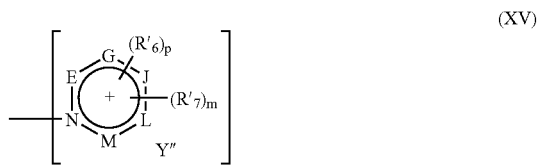

wherein:
the ring members E, G, J and L, which may be identical or different, are chosen from carbon, oxygen, sulfur and nitrogen atoms, to form a pyrrole, pyrazole, imidazole, triazole, oxazole, isooxazole, thiazole or isothiazole ring;
q is an integer ranging from 0 to 4;
o is an integer ranging from 0 to 3;
the sum of q and o is an integer ranging from 0 to 4;
R₇, which may be identical or different, are chosen from hydroxyl radicals, $C_1$–$C_6$ alkyl radicals, $C_1$–$C_6$ monohydroxyalkyl radicals, $C_2$–$C_6$ polyhydroxyalkyl radicals, $C_1$–$C_6$ alkoxy radicals and tri($C_1$–$C_6$-alkyl)silane ($C_1$–$C_6$-alkyl) radicals; wherein the radicals R₇ are borne by a carbon atom R₆, which may be identical or different, are chosen from $C_1$–$C_6$ alkyl radicals, $C_1$–$C_6$ monohydroxyalkyl radicals, $C_2$–$C_6$ polyhydroxyalkyl radicals, tri($C_1$–$C_6$-alkyl)silane($C_1$–$C_6$-alkyl) radicals, ($C_1$–$C_6$-alkoxy)($C_1$–$C_6$-alkyl) radicals, carbamyl($C_1$–$C_6$-alkyl) radicals, ($C_1$–$C_6$-alkyl)carboxy($C_1$–$C_6$-alkyl) radicals and benzyl radicals; wherein the radicals R₆ are borne by a nitrogen; and $Y_1'$ is a counterion.

14. The process as claimed in claim 13, wherein the ring members E, G, J and L form a ring chosen from pyrrole, imidazole, pyrazole, oxazole, thiazole and triazole rings.

15. The process as claimed in claim 14, wherein the ring members E, G, J and L form an imidazole ring.

16. The process as claimed in claim 1, wherein in formula (I), R₂ is an onium radical of formula (XV):

where:
the ring members E, G, J, L and M, which may be identical or different, are chosen from carbon, oxygen, sulfur and nitrogen atoms, to form a ring selected from pyridine, pyrimidine, pyrazine, triazine and pyridazine rings;
p is an integer ranging from 0 to 3;
m is an integer ranging from 0 to 5 inclusive;
the sum of p and m is an integer ranging from 0 to 5;
R′₇, which may be identical or different, are chosen from hydroxyl radicals, $C_1$–$C_6$ alkyl radicals, $C_1$–$C_6$ monohydroxyalkyl radicals, $C_2$–$C_6$ polyhydroxyalkyl radicals, $C_1$–$C_6$ alkoxy radicals and tri($C_1$–$C_6$-alkyl)silane ($C_1$–$C_6$-alkyl) radicals; wherein the radicals R′₇ are borne by a carbon atom;
R′₆, which may be identical or different, are chosen from $C_1$–$C_6$ alkyl radicals, $C_1$–$C_6$ monohydroxyalkyl radicals, $C_2$–$C_6$ polyhydroxyalkyl radicals, tri($C_1$–$C_6$-alkyl)silane($C_1$–$C_6$-alkyl) radicals, ($C_1$–$C_6$-alkoxy)($C_1$–$C_6$-alkyl) radicals, carbamyl($C_1$–$C_6$-alkyl) radicals, ($C_1$–$C_6$-alkyl)carboxy($C_1$–$C_6$-alkyl) radicals and benzyl radicala; wherein the radicals R′₆ are borne by a nitrogen; and Y″ is a counterion.

17. The process as claimed in claim 16, wherein the ring members E, G, J, L and M form, with the nitrogen of the ring, a ring chosen from pyridine and pyrimidine rings.

18. The process as claimed in claim 13, wherein R₆, R₇, which may identical or different, are chosen from alkyl radicals, which may be substituted.

19. The process as claimed in claim 16, wherein R′₇ and R′₆, which may identical or different, are chosen from alkyl radicals, which may be substituted.

20. The process as claimed in claim 1, wherein the compound of formula (I) is chosen from the list below:

| Nomenclature | Structure |
|---|---|
| [1-(4-Aminophenyl)-pyrrolidin-3-yl]-3-methyl-1H-imidazol-3-ium chloride, hydrochloride | H₂N—C₆H₄—N(pyrrolidine)—(N-imidazolium-N⁺—CH₃) Cl⁻, xHCl |
| [1-(4-Aminophenyl)-pyrrolidin-3-yl]trimethyl-ammonium chloride, hydrochloride | H₂N—C₆H₄—N(pyrrolidine)—N⁺(CH₃)₃ Cl⁻, xHCl |
| 1-(4-Aminophenyl)-pyrrolidine-3-amine dihydrochloride | H₂N—C₆H₄—N(pyrrolidine)—NH₂, xHCl |
| 1-(4-Aminophenyl)-N,N-dihydroxyethylpyrrolidine-3-amine dihydrochloride | H₂N—C₆H₄—N(pyrrolidine)—N(CH₂CH₂OH)₂, xHCl |
| [1-(4-Aminophenyl)-pyrrolidin-3-yl]pyridinium chloride, hydrochloride | H₂N—C₆H₄—N(pyrrolidine)—N⁺(pyridinium) Cl⁻, xHCl |
| [1-(4-Aminophenyl)-pyrrolidin-3-yl]methyl-piperidinium chloride, hydrochloride | H₂N—C₆H₄—N(pyrrolidine)—N⁺(piperidinium)(CH₃) Cl⁻, xHCl |
| 1-(4-Aminophenyl)-N-methylpyrrolidine-3-amine dihydrochloride | H₂N—C₆H₄—N(pyrrolidine)—NHCH₃, xHCl |
| 1-(4-Aminophenyl)-N,N-dimethylpyrrolidine-3-amine dihydrochloride | H₂N—C₆H₄—N(pyrrolidine)—N(CH₃)₂, xHCl |
| 1-(4-Amino-3-methylphenyl)-pyrrolidine-3-amine dihydrochloride | H₂N—(3-methyl-C₆H₃)—N(pyrrolidine)—NH₂, xHCl |
| [1-(4-Amino-3-methyl-phenyl)pyrrolidin-3-yl]-trimethylammonium chloride, hydrochloride | H₂N—(3-methyl-C₆H₃)—N(pyrrolidine)—N⁺(CH₃)₃ Cl⁻, xHCl |

| Nomenclature | Structure |
|---|---|
| [1-(4-Amino-3-methyl-phenyl)pyrrolidin-3-yl]-3-methyl-1H-imidazol-3-ium chloride, hydrochloride | , xHCl |
| 1-(4-Amino-3-methylphenyl)-N,N-di-hydroxyethyl-pyrrolidine-3-amine dihydrochloride | , xHCl |
| 1-(4-Aminophenyl)-pyrrolidine-3-amino-guanidine dihydrochloride | , xHCl |

21. The process as claimed in claim 1, wherein step d) further comprises a reduction step.

22. The process as claimed in claim 21, wherein the reduction step is chosen from hydrogenation and hydrolysis.

* * * * *